*(12)* United States Patent
Spencer et al.

(10) Patent No.: US 9,733,219 B2
(45) Date of Patent: Aug. 15, 2017

(54) AUTOMATED WELD INSPECTION SYSTEM WITH WELD ACCEPTABILITY PASS OR FAIL INDICATIONS

(71) Applicant: EWI, INC., Columbus, OH (US)

(72) Inventors: Roger Spencer, Ashville, OH (US); Bill Colgan, Columbus, OH (US); Paul C. Boulware, Columbus, OH (US); Ron Brown, Columbus, OH (US); Jeong K. Na, Centerville, OH (US); Scott A. Newhouse, Columbus, OH (US)

(73) Assignee: Cumberland & Western Resources, LLC, Bowling Green, KY (US)

( * ) Notice: Subject to any disclaimer, the term of this patent is extended or adjusted under 35 U.S.C. 154(b) by 226 days.

(21) Appl. No.: 14/719,427

(22) Filed: May 22, 2015

(65) Prior Publication Data
US 2015/0253288 A1     Sep. 10, 2015

Related U.S. Application Data

(63) Continuation-in-part of application No. 13/468,502, filed on May 10, 2012, now Pat. No. 9,063,059.
(Continued)

(51) Int. Cl.
*G01N 9/24*     (2006.01)
*G01N 29/24*     (2006.01)
(Continued)

(52) U.S. Cl.
CPC ......... *G01N 29/24* (2013.01); *G01N 29/0645* (2013.01); *G01N 29/11* (2013.01);
(Continued)

(58) Field of Classification Search
CPC ................. G01N 29/075; G01N 29/24; G01N 2291/0234; G01N 2291/2672;
(Continued)

(56) References Cited

U.S. PATENT DOCUMENTS

| 4,208,917 A | * | 6/1980 | Aoyama | G01N 29/221 |
| | | | | 73/588 |
| 5,142,649 A | * | 8/1992 | O'Donnell | G10K 11/346 |
| | | | | 367/7 |

(Continued)

*Primary Examiner* — Laura Martin
*Assistant Examiner* — Samir M Shah
(74) *Attorney, Agent, or Firm* — Frost Brown Todd LLC

(57) ABSTRACT

An automated system for non-destructively evaluating spot welds that includes at least one matrix phased array probe; a fixture adapted to be mounted on a robot or other mechanical actuator, wherein the fixture is further adapted to retain the at least one matrix phased array probe; and an enclosure that includes at least one input for connecting to the at least one matrix phased array probe, ultrasonic phased array transmitting and receiving circuitry in electrical communication with the at least one input, at least one data processor running software that includes at least one algorithm for processing data received from the probe and generating discrete specifications of evaluated welds, wherein the discrete specifications further include pass indications or fail indications regarding weld acceptability; and at least one output for outputting the discrete specifications of evaluated welds.

30 Claims, 11 Drawing Sheets

Related U.S. Application Data

(60) Provisional application No. 61/484,312, filed on May 10, 2011, provisional application No. 62/149,858, filed on Apr. 20, 2015.

(51) Int. Cl.
  *G01N 29/06* (2006.01)
  *G01N 29/26* (2006.01)
  *G01N 29/28* (2006.01)
  *G01N 29/11* (2006.01)
  *G01N 29/30* (2006.01)

(52) U.S. Cl.
  CPC ........... *G01N 29/262* (2013.01); *G01N 29/28* (2013.01); *G01N 29/30* (2013.01); *G01N 2291/0234* (2013.01); *G01N 2291/106* (2013.01); *G01N 2291/2638* (2013.01); *G01N 2291/2672* (2013.01)

(58) Field of Classification Search
  CPC ......... G01N 2291/0289; G01N 29/262; G01N 29/30; G01N 29/0645; G01N 2291/2638
  See application file for complete search history.

(56) References Cited

U.S. PATENT DOCUMENTS

| | | | | |
|---|---|---|---|---|
| 5,331,964 A * | 7/1994 | Trahey | ................ | G01S 7/52049 600/443 |
| 5,674,415 A * | 10/1997 | Leong | ................ | B23K 26/032 219/121.63 |
| 6,813,950 B2 * | 11/2004 | Glascock | ............ | G01N 29/221 73/622 |
| 6,925,882 B1 * | 8/2005 | Fleming | ................ | B23K 31/12 73/632 |
| 6,948,369 B2 * | 9/2005 | Fleming | ................ | G01N 3/00 228/104 |
| 7,021,143 B2 * | 4/2006 | Dasch | ................ | G01N 29/225 73/620 |
| 7,132,617 B2 * | 11/2006 | Lee | ................ | B23K 11/24 219/109 |
| 7,448,272 B2 * | 11/2008 | Aznar | ................ | G01N 29/11 73/634 |
| 7,516,022 B2 * | 4/2009 | Lee | ................ | B23K 11/24 702/187 |
| 7,698,944 B2 * | 4/2010 | Takada | ................ | G01N 29/041 73/588 |
| 7,775,415 B2 * | 8/2010 | Maev | ................ | G01N 29/262 219/91.1 |
| 8,146,429 B2 * | 4/2012 | Ume | ................ | G01N 29/11 73/599 |
| 8,215,173 B2 * | 7/2012 | Spencer | ................ | G01N 29/069 73/620 |
| 8,297,122 B2 * | 10/2012 | Ume | ................ | G01N 29/07 73/600 |
| 9,063,059 B2 * | 6/2015 | Na | ................ | G01N 29/0645 |
| 2003/0234239 A1 * | 12/2003 | Lee | ................ | B23K 11/24 219/109 |
| 2004/0020298 A1 * | 2/2004 | Siverling | ................ | G01N 29/275 73/644 |
| 2004/0245315 A1 * | 12/2004 | Maev | ................ | G01N 29/262 228/8 |
| 2005/0126293 A1 * | 6/2005 | Dasch | ................ | G01N 29/225 73/618 |
| 2005/0132809 A1 * | 6/2005 | Fleming | ................ | G01N 3/00 73/597 |
| 2007/0240512 A1 * | 10/2007 | Takada | ................ | G01N 29/041 73/588 |
| 2008/0196504 A1 * | 8/2008 | Johnson | ................ | G21C 17/007 73/588 |
| 2009/0133501 A1 * | 5/2009 | Georgeson | ................ | G01N 29/04 73/632 |
| 2010/0031750 A1 * | 2/2010 | Spencer | ................ | G01N 29/069 73/620 |
| 2012/0310551 A1 * | 12/2012 | Na | ................ | G01N 29/0645 702/39 |
| 2014/0165730 A1 * | 6/2014 | Na | ................ | G01N 29/0645 73/588 |
| 2016/0231291 A1 * | 8/2016 | Boulware | ................ | G01N 29/262 |
| 2016/0320344 A1 * | 11/2016 | Spencer | ................ | G01N 29/043 |

* cited by examiner

3-Dimensional Array Element

AUTOMATED WELD INSPECTION SYSTEM WITH WELD ACCEPTABILITY PASS OR FAIL INDICATIONS

CROSS-REFERENCE TO RELATED APPLICATIONS

This patent application is a continuation-in-part of U.S. patent application Ser. No. 13/468,502 filed on May 10, 2012 and entitled "3-D Matrix Phased Array Spot Weld Inspection System", which claimed the benefit of U.S. Provisional Patent Application Ser. No. 61/484,312 filed on May 10, 2011 and entitled "Three-Dimensional Matrix Phased Array Spot Weld Inspection System", the disclosures of which are incorporated by reference herein in their entirety and made part of the present U.S. utility patent application for all purposes. This patent application also claims the benefit of U.S. Provisional Patent Application Ser. No. 62/149,858 filed on Apr. 20, 2015 and entitled "Automated Weld Inspection System," the disclosure of which is hereby incorporated by reference herein in its entirety and made part of the present U.S. utility patent application for all purposes.

BACKGROUND OF THE INVENTION

The present invention relates generally to inspection systems for use in assessing the performance of industrial manufacturing processes, and more specifically to a nondestructive inspection system for assessing the quality of resistance spot welds and other weld joints.

Sheet metal joining processes are widely used in many industries including the aerospace and automotive industries. Among these processes, resistance spot welding is a very common procedure used to join metal sheets because it has high process speed and is easily adopted in mass production lines. Seam welding, weld bonding, adhesive joining, soldering, and brazing have also gained acceptance. The quality control of such joining processes has been recognized as an important issue to manufacturers. The quality of weld joints is affected by the joining process itself and by the design of the joint. Many factors are considered, including metallurgic reactions, thermal behaviors, chemical composition, starting condition of the base metal, welding and bonding conditions, and the welding and bonding equipment used during the process. Furthermore, the intricate relationship between these factors makes it difficult to control the quality of the weld joint and difficult to inspect the weld joint in a nondestructive manner.

Acoustic methods are commonly used nondestructive testing methods for various inspection applications. Unlike other nondestructive testing methods, acoustic methods provide both surface and internal information. Moreover, acoustic methods allow for deeper penetration into specimens and higher sensitivity to small discontinuities in a weld joint. Acoustic methods, however, do have limitations. The most significant limitations include the requirement of a skillful operator for using the testing device and analyzing acoustic data, as well as the very subjective nature of identifying a stuck or cold weld or inadequate bond, such as a kissing bond. Accordingly, the field of ultrasonic nondestructive evaluation (NDE) is in need of a reliable system and method for identifying poor quality joints in a manner that eliminates the involvement of a skilled operator and the subjective interpretation of test data derived from the inspection. Furthermore, there is an ongoing need for an automated system for conducting weld inspection that provides rapid, efficient, and reliable characterization and evaluation of spot welds and other welds.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first portable system for non-destructively characterizing a spot weld is provided. This system includes at least one matrix phased array probe, a fixture, and an enclosure. The matrix phased array probe further includes a plurality of ultrasonic transducer elements arranged in a curved array at one end of the probe that are operative to both generate ultrasonic signals and to receive reflections thereof; and a combination of materials for allowing the probe to conform to a contoured surface of the spot weld while enabling sound energy to be transferred directly into the spot weld under test conditions, wherein the combination of materials further includes a flexible membrane mounted on the end of the probe and a fluid filled chamber or solid sound delay material disposed between the membrane and the array. The fixture is adapted to be mounted on a robot or other mechanical actuator, and to retain the at least one matrix phased array probe. The enclosure includes at least one input for connecting to the at least one matrix phased array probe; ultrasonic phased array transmitting and receiving circuitry in electrical communication with the at least one input; at least one data processor running software that includes at least one algorithm for processing data received from the probe and generating discrete specifications of evaluated welds, wherein the discrete specifications further include pass indications or fail indications regarding weld acceptability; and at least one output for outputting the discrete specifications of evaluated welds.

In accordance with another aspect of the present invention, a second portable system for non-destructively characterizing a spot weld is provided. This system also includes at least one matrix phased array probe, a fixture, and an enclosure. The matrix phased array probe further includes a plurality of ultrasonic transducer elements arranged in a curved array at one end of the probe, wherein the transducer elements are operative to both generate ultrasonic signals and to receive reflections thereof; and wherein the transducer elements are further arranged into discrete subgroups, and wherein each subgroup may be activated independently of the other subgroups and at different time intervals; and a combination of materials for allowing the probe to conform to a contoured surface of the spot weld while enabling sound energy to be transferred directly into the spot weld under test conditions, wherein the combination of materials further includes a flexible membrane mounted on the tip of the probe and a fluid filled chamber or solid sound delay material disposed between the membrane and the array. The fixture is adapted to be mounted on a robot or other mechanical actuator and to retain the at least one matrix phased array probe, wherein the robot or other mechanical actuator is operative to move the probe through a predetermined range of positions, and wherein the predetermined range of positions is operative to facilitate the production of high-integrity scans or images of welds being characterized. The enclosure includes at least one input for connecting to the at least one matrix phased array probe; ultrasonic phased array transmitting and receiving circuitry in electrical communication with the at least one input; at least one data processor running software that includes at least one algorithm for processing data received from the probe and generating discrete specifications of evaluated welds, wherein the discrete specifications further include pass indications or fail indications regarding weld acceptability; and at least one output for outputting the discrete specifications of evaluated welds.

In yet another aspect of this invention, a third portable system for non-destructively characterizing a spot weld is provided. This system also includes at least one matrix phased array probe, a fixture, and a control enclosure. The matrix phased array probe further includes a plurality of ultrasonic transducer elements arranged in a curved array at one end of the probe, wherein the transducer elements are operative to both generate ultrasonic signals and to receive reflections thereof; and wherein the transducer elements are further arranged into discrete subgroups, and wherein each subgroup may be activated independently of the other subgroups and at different time intervals; and a combination of materials for allowing the probe to conform to a contoured surface of the spot weld while enabling sound energy to be transferred directly into the spot weld under test conditions, wherein the combination of materials further includes a flexible membrane mounted on the tip of the probe and a fluid filled chamber or solid sound delay material disposed between the membrane and the array; and wherein the tip of the probe is pre-filled with couplant and further includes a quick-connect disconnect mechanism for rapidly detaching and reattaching the tip to the probe. The fixture is adapted to be mounted on a robot or other mechanical actuator and to retain the at least one matrix phased array probe, wherein the robot or other mechanical actuator is operative to move the probe through a predetermined range of positions, and wherein the predetermined range of positions is operative facilitate the production of high-integrity scans and/or images of welds being characterized. The enclosure includes at least one input for connecting to the at least one matrix phased array probe; ultrasonic phased array transmitting and receiving circuitry in electrical communication with the at least one input; at least one data processor running software that includes at least one algorithm for processing data received from the probe and generating discrete specifications of evaluated welds, wherein the discrete specifications further include pass indications or fail indications regarding weld acceptability; and at least one output for outputting the discrete specifications of evaluated welds.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Figure 1:
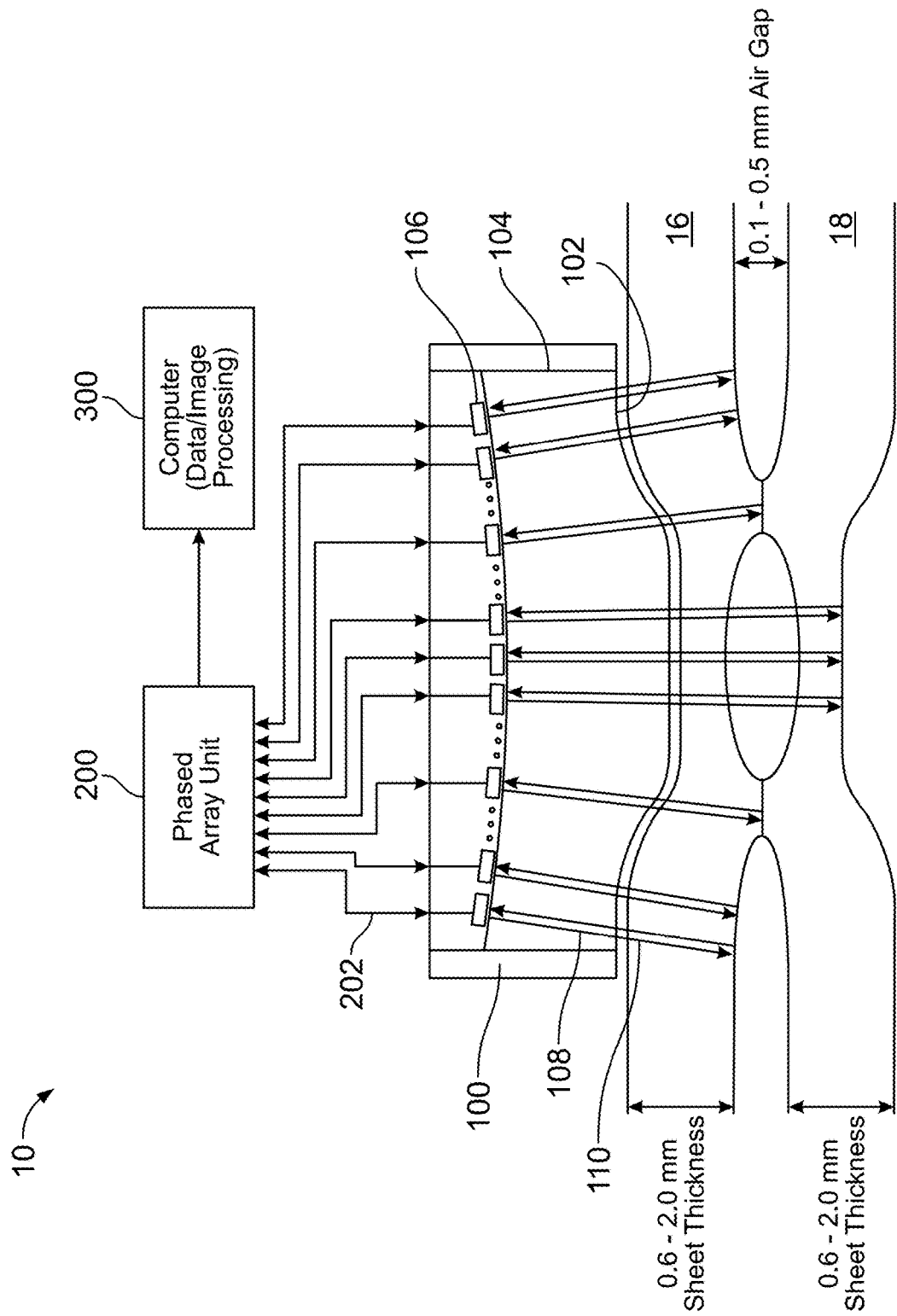
FIG. 1 is a block diagram showing the primary components of a three-dimensional matrix phased array spot weld inspection system in accordance with an exemplary embodiment of the present invention.

Exemplary embodiments of the present invention are now described with reference to the Figures. Reference numerals are used throughout the detailed description to refer to the various elements and structures. In other instances, well-known structures and devices are shown in block diagram form for purposes of simplifying the description. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present application incorporates by reference herein U.S. patent application Ser. Nos. 12/186,047; 13/468,502; and 14/183,643, in their entirety for all purposes. With regard to the nomenclature used herein, the present invention is described as being useful for analyzing the integrity of a resistance spot weld between a first and second workpiece or upper and lower sheets of metal. However, this invention is applicable to all welds regardless of material, configuration, or the number of workpieces, as well as adhesive bonds. Thus, while the present disclosure generally refers to a stuck weld, one skilled in the art will appreciate that the present invention detects stuck portions of joints, which are often referred to as kissing bonds or weak bonds in the field of adhesives. This invention is also applicable to metals and nonmetals alike and is not limited to fusion welding, but may also be used to examine solid state welds, brazed and soldered joints. Thus, while this method has particular application in the automated analysis of spot welds, it may also be used to evaluate continuous bonds.

A stuck weld or stuck joint occurs when workpieces (e.g., pieces of sheet metal) are held together by localized fusion at the welding interface, but no weld button or weld nugget has formed as a result of the welding process. A stuck weld typically results from heat at the welding interface being insufficient to create nugget growth. In the absence of a properly formed weld nugget, fusion may occur at certain points of contact between the sheets of metal. With coated materials, coatings can melt and refreeze, effectively soldering the parts together. The resulting bonds are often strong enough to hold the workpieces together under light loads, but reasonable force will pull them apart. If ultrasonic testing is used to analyze weld integrity, transmitted ultrasonic beams (i.e., sound waves) will not pass through the interface between sheets if no fusion has occurred. If a stuck weld as occurred, resulting in fusion, but no weld nugget, transmitted ultrasonic beams will pass partially though the sheet interface. If a weld nugget has been properly formed, transmitted ultrasonic beams will pass completely through the sheet interface.

Phased Array Ultrasonic Testing (PAUT) may be used for flaw detection, sizing, and imaging. PAUT technology is the ability to modify electronically the acoustic probe characteristics. Probe modifications are performed by introducing time shifts in the signals sent to (pulse) and received from (echo) individual elements of an array probe. Three common formats for collecting and displaying ultrasonic data for purposes of non-destructive evaluation are A-scan, B-scan and C-scan presentations. Each presentation mode provides a means for visualizing and evaluating the region of material being inspected. An A-scan is a simple RF waveform presentation showing the time and amplitude of an ultrasonic signal, as commonly provided by conventional ultrasonic flaw detectors and waveform display thickness gages. A-scan is an amplitude modulation scan, and as generally applied to pulse echo ultrasonics, horizontal and vertical sweeps are proportional to time or distance and amplitude or magnitude respectively. Thus the location and magnitude of acoustical interface are indicated as to depth below the transducer. The relative amount of energy received is plotted along the vertical axis and the elapsed time (which may be related to the sound energy travel time within the material) is displayed along the horizontal axis. Most instruments utilizing an A-scan display allow the signal to be displayed in its natural radio frequency form (RF) as a fully rectified RF signal or as either the positive or negative half of the RF signal. In the A-scan presentation, relative discontinuity size can be estimated by comparing the signal amplitude obtained from an unknown reflector to that from a known reflector. Reflector depth can be determined by the position of the signal on the horizontal sweep. A C-scan from a phased array system involves an ultrasonic probe being physically moved along one axis while the beam electronically scans along the other axis according to the focal law sequence. Signal amplitude or depth data is collected within gated regions of interest. Data is plotted with each focal law progression, using the programmed beam aperture. Utilizing a matrix phased array probe, beam steering can be accomplished in multiple directions.

With reference to the Figures, an exemplary embodiment of the present invention provides a nondestructive inspection system for assessing the quality of resistance spot welds. As shown in FIG. 1, which is a block diagram of an exemplary embodiment, spot weld inspection system 10, is operative to assess the quality of weld 12, which is formed at interface 14, which is located between upper sheet 16 and lower sheet 18 (both having a sheet thickness of about 0.6 mm to about 2.0 mm). An air gap of about 0.1 mm to about 0.5 mm may be present between upper sheet 16 and lower sheet 18. A three-dimensional, matrix phased array probe 100 is placed on the region of upper sheet 16 that is located over the welded area. A curved array of ultrasonic elements 106 is used to transmit a plurality of ultrasonic beams 108 into the welded area and to capture the associated reflections 110 of those ultrasonic beams. Phased array unit 200 is in electrical communication with the plurality of ultrasonic elements 102 through a plurality of signal pathways 202. Phased array unit 200 is also in electrical communication with computer 300, which processes incoming ultrasonic data and generates a visual representation of the welded area. Probe 100 includes flexible membrane 102, which allows the tip of the probe to conform to the contour of the welded area and fluid filled chamber 104 or solid sound delay material for focusing and steering ultrasonic beams 108. Because flexible membrane 102 is capable of conforming to curved surfaces as shown in FIG. 1, and because the array of transducer elements 106 is configured in a curved geometry (see FIG. 1), the matrix phased array system of this invention is referred to as "three-dimensional" as opposed a "two-dimensional" system which uses a probe having a flattened array and a flat tip.

Figure 2A:
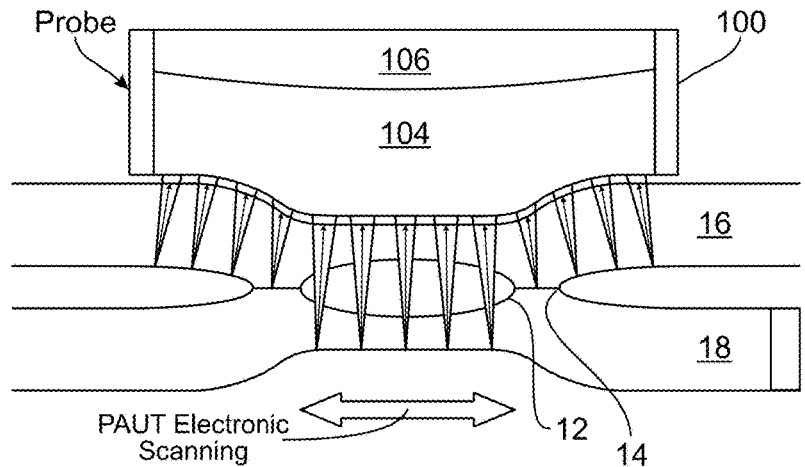
FIGS. 2a-c provide illustrations of test results derived from analyzing a good spot weld using the system of FIG. 1.
Figure 2B:
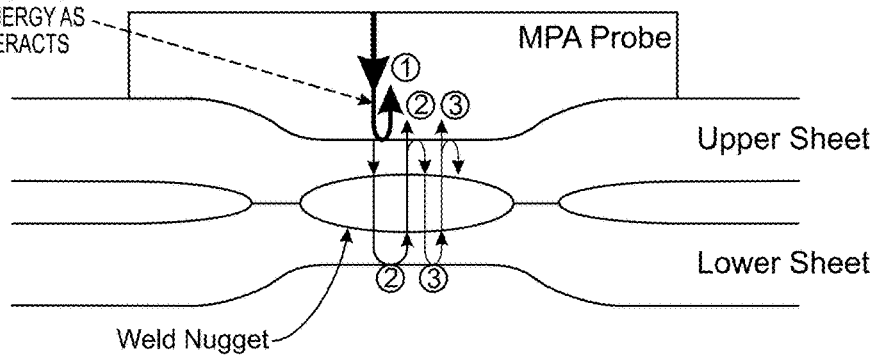
Figure 2C:
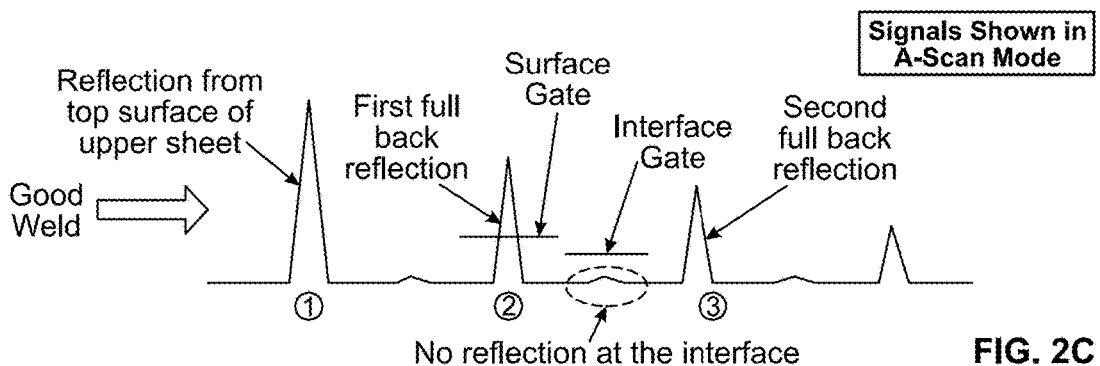
Figure 3:
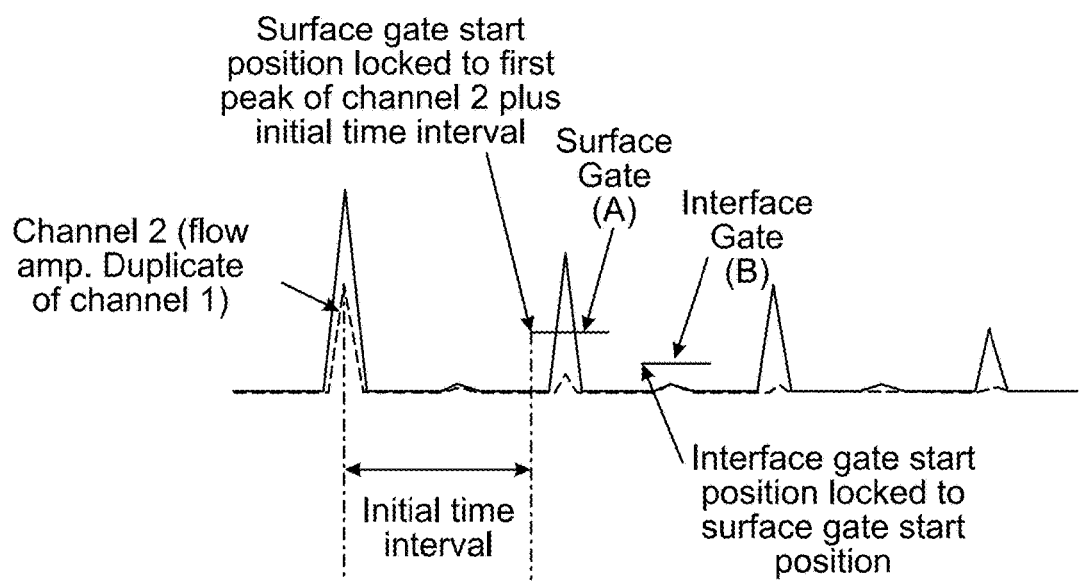
FIG. 3 provides a visual representation in A-scan mode of the electronic gates included in the weld inspection system of FIG. 1.

FIGS. 2a-c provide illustrations of test results derived from analyzing a good spot weld using system 10. In FIG. 2a, ultrasonic beams travel completely through weld 12 and interface 14 and reflect back to probe 100 from the backside of lower sheet 18. FIG. 2b illustrates diagrammatically the direction and relative strength of each sound wave as it transmits and reflects at interface 14. In FIG. 2b, a thinner line represents loss of acoustic energy as the sound wave interacts with interface 14. The reflected signals designated as circled 1, 2, and 3 correspond to the peaks shown in the A-scan presented in FIG. 2c. FIG. 2c provides the signals derived from testing in A-scan mode, wherein signal 1 represents the reflection from the top surface of upper sheet 16, signal 2 represents the first full back reflection, and signal 3 represents the second full back reflection. The horizontal line drawn through signal 2 represents a surface gate and the horizontal line adjacent to signal 2 represents an interface gate (see discussion below.)

Based on the ultrasonic energy transmission and reflection at weld interface 14 and the back side of lower sheet 18, system 10 uses two adjustable electronic gates to filter out all unwanted reflected signals. The two signals that pass through the gates are either the reflected signal from the back side of the second sheet of metal or the reflected signal from the interface of the two sheet metals. The first gate is called the "surface gate" and the second gate is called the "interface gate". This approach differs from the current commercially available systems that utilize an attenuation coefficient compensation method. In such systems, multiple reflections from all of surfaces and the interface are taken into account to determine attenuation coefficients and make a correction for acoustic energy loss caused by the spot weld fusion, assuming that the microstructure of fused section of the spot weld has a higher attenuation coefficient compared to a stuck weld condition. As disclosed and claimed in U.S. patent application Ser. No. 12/186,047, which is incorporated by reference herein, each ultrasonic element in array 106 generates a primary ultrasonic beam and a secondary ultrasonic beam wherein the primary ultrasonic beam is high gain and wherein the secondary ultrasonic beam is low gain; and wherein the primary and secondary ultrasonic beams are fired in within very close proximity to one another (i.e., milliseconds). As shown in FIG. 4, channel 2 is a low amplitude duplicate of channel 1 in each peak. The initial time interval shown is measured from the center of the first peak to the surface gate start position. The surface gate start position is locked to the first peak of channel 2 plus the initial time interval. The interface gate start position is locked to the surface gate start position. System 10 measures the ration of signal amplitude (height) between gate A and B and only signals between the gate start and end positions are considered.

Figure 4A:
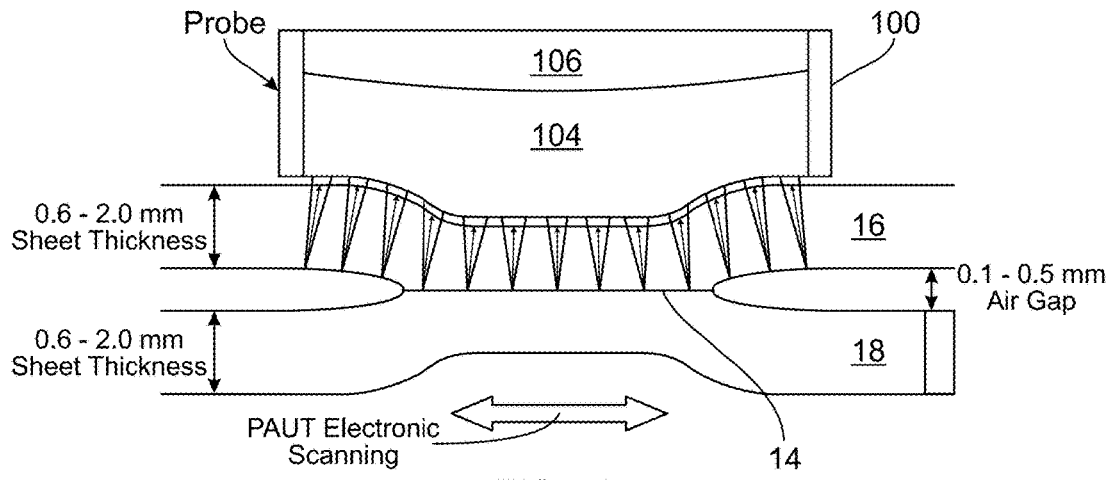
FIGS. 4a-c provide illustrations of test results derived from analyzing a poor spot weld using the system of FIG. 1.
Figure 4B:
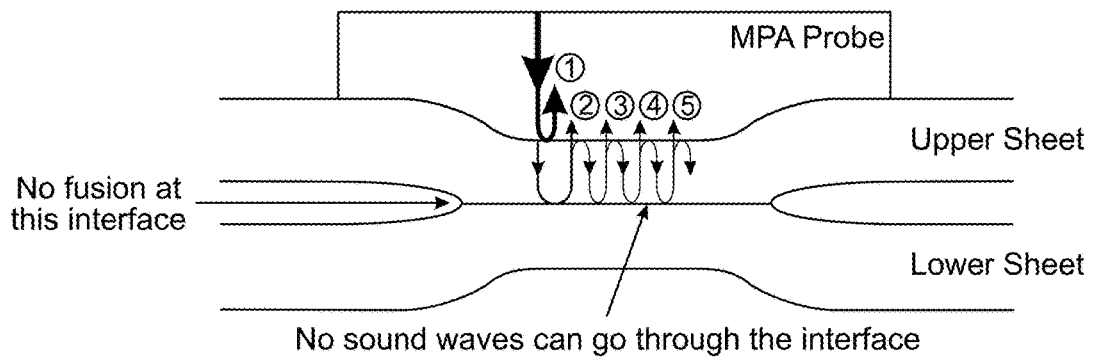
Figure 4C:
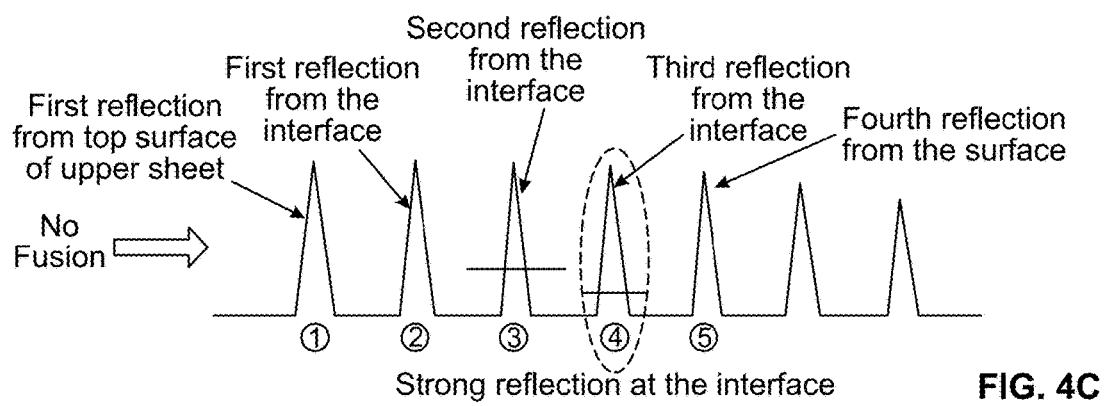

FIGS. 4*a-c* provide illustrations of test results derived from analyzing a poor spot weld using system 10. In FIG. 4*a*, because no weld nugget exists, ultrasonic beams do not travel completely through interface 14, but rather reflect back to probe 100 from interface 14. FIG. 4*b* illustrates diagrammatically the direction and relative strength of each sound wave as it reflects at interface 14. In FIG. 4*b*, a thinner line represents loss of acoustic energy as the sound wave interacts with interface 14. The reflected signals designated as circled 1, 2, 3, 4, and 5 correspond to the peaks shown in the A-scan presented in FIG. 4*c*. FIG. 4*c* provides the signals derived from testing in A-scan mode, wherein signal 1 represents the first reflection from the top surface of upper sheet 16, signal 2 represents the first reflection from interface 14, signal 3 represents the second reflection from interface 14, signal 4 represents the third reflection from interface 14, and signal 5 represents the fourth reflection from interface 14. The horizontal line drawn through signal 3 represents the surface gate and the horizontal line drawn though signal 4 represents the interface gate (see discussion above.)

Figure 5A:
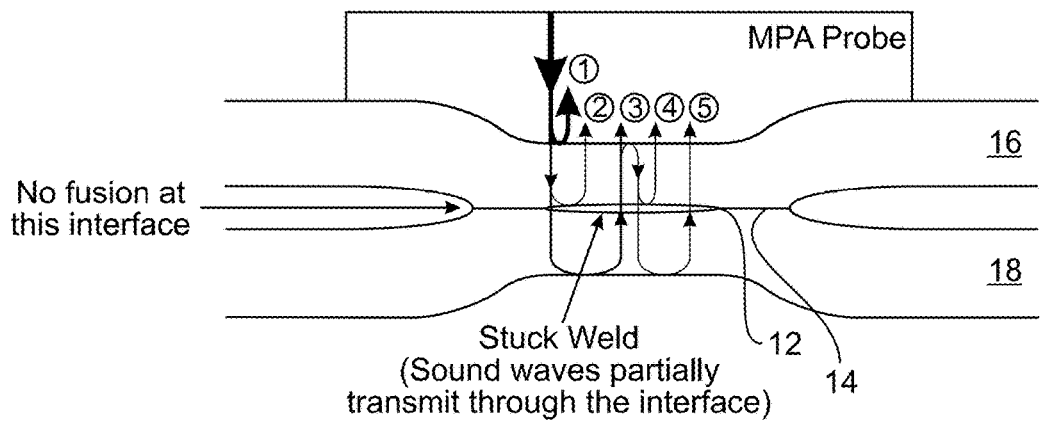
FIGS. 5a-b provide illustrations of test results derived from analyzing a stuck weld using the system of FIG. 1.
Figure 5B:
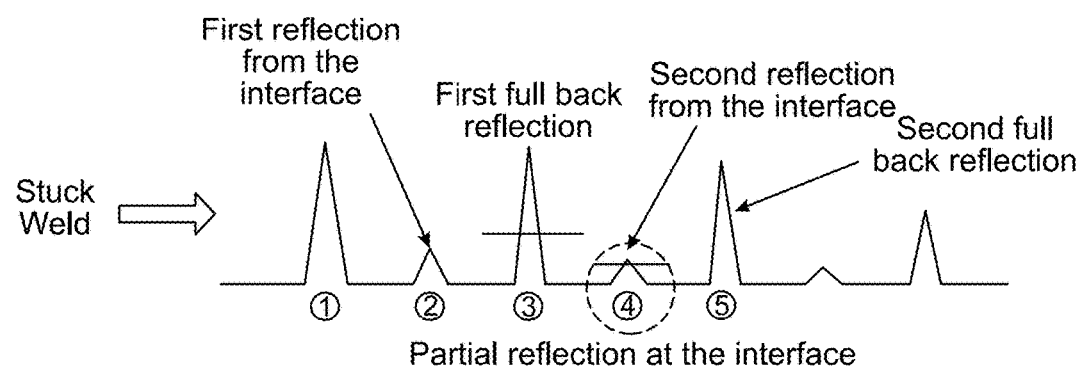

FIGS. 5*a-b* provide illustrations of test results derived from analyzing a stuck weld using system 10. Because an incomplete or poorly formed weld exists, ultrasonic beams travel only partially through interface 14, while intermediate echoes appear between the echoes of interface 14 and full back wall reflection. FIG. 5*a* illustrates diagrammatically the direction and relative strength of each sound wave as it transmits and reflects at interface 14. In FIG. 5*a*, a thinner line represents loss of acoustic energy as the sound wave interacts with interface 14. The reflected signals designated as circled 1, 2, 3, 4, and 5 correspond to the peaks shown in the A-scan presented in FIG. 5*b*. FIG. 5*b* provides the signals derived from testing in A-scan mode, wherein signal 2 represents the first reflection from interface 14, signal 3 represents the first full back reflection, signal 4 represents the second reflection from interface 14, and signal 5 represents the second full back reflection. The horizontal line drawn through signal 3 represents the surface gate and the horizontal line drawn though signal 4 represents the interface gate (see discussion above.)

Figure 6A:
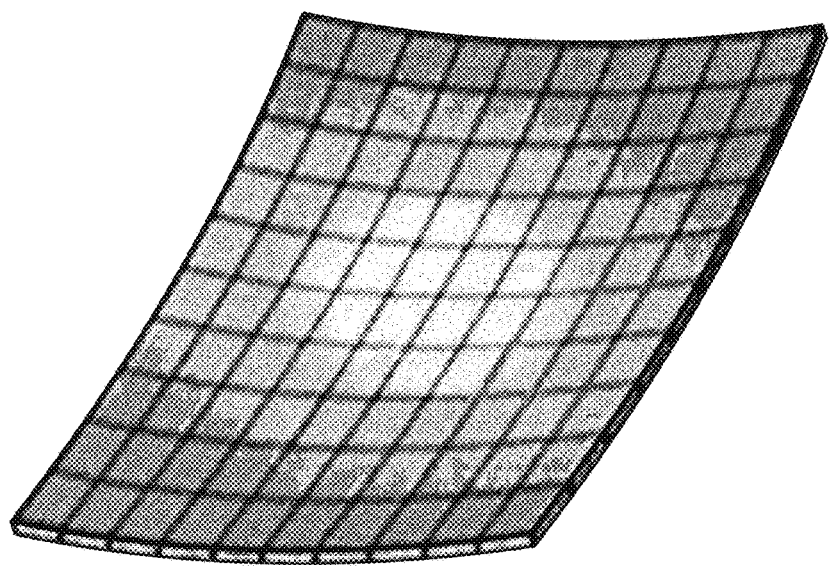
FIGS. 6a-b illustrate the shape of the 3-D curved probe element as well as various firing sequences for the sub-element groups.
Figure 6B:
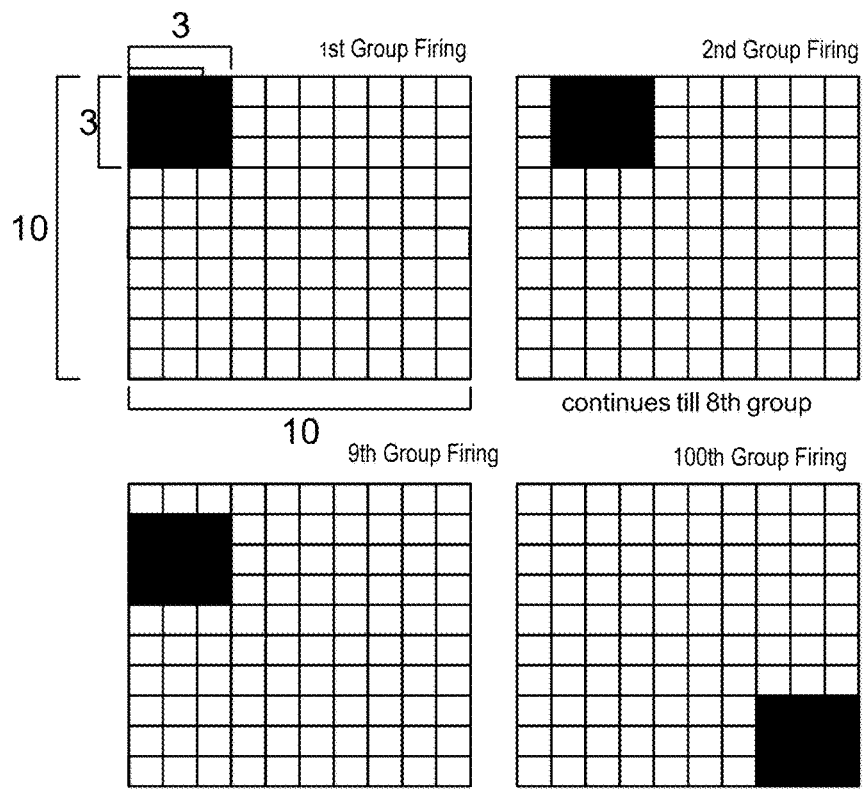

FIGS. 6*a-b* illustrate the geometry of the curved three-dimensional probe element (FIG. 6*a*) as well as various firing sequences for the sub-element groups (FIG. 6*b*). Acoustic probe 100 includes a plurality of ultrasonic transducer elements 106 arranged in a three-dimensional array and having a combination of materials for allowing the probe to conform to the contoured surface of a spot weld while enabling the sound energy to be transferred directly into the spot weld under test. An excitation element (phased array unit 200) is coupled to the array and a subset group of transducer elements are combined to send an ultrasonic beam toward a spot weld. Each transducer element in a subset group may be pulsed at different time intervals (phase delay) and their individual waves summed to produce a focusing effect of the beam as well as a steering effect. Other three-dimensional arrangements are possible for optimizing the performance for specific applications. The total number of elements, overall dimension, and operating frequency determine the overall three-dimensional surface contour shape and its operating characteristics and parameters.

Figure 7A:
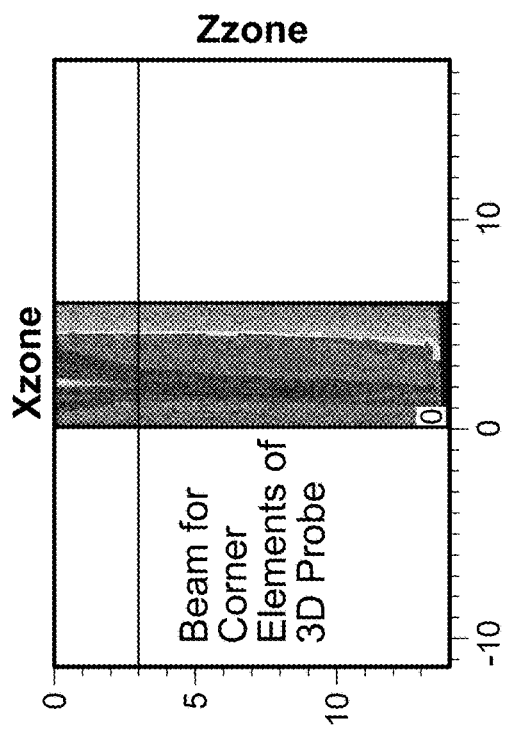
FIGS. 7a-d provide modeling verification of the benefits of a 3-D curved probe design versus a 2-D flat probe design.
Figure 7B:
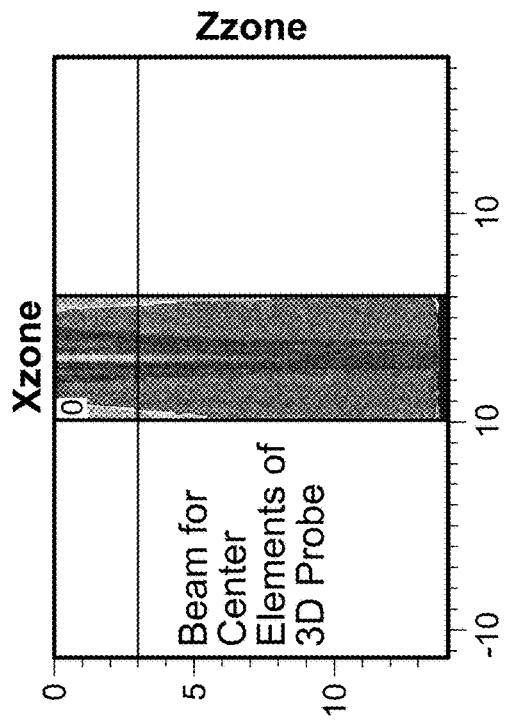
Figure 7C:
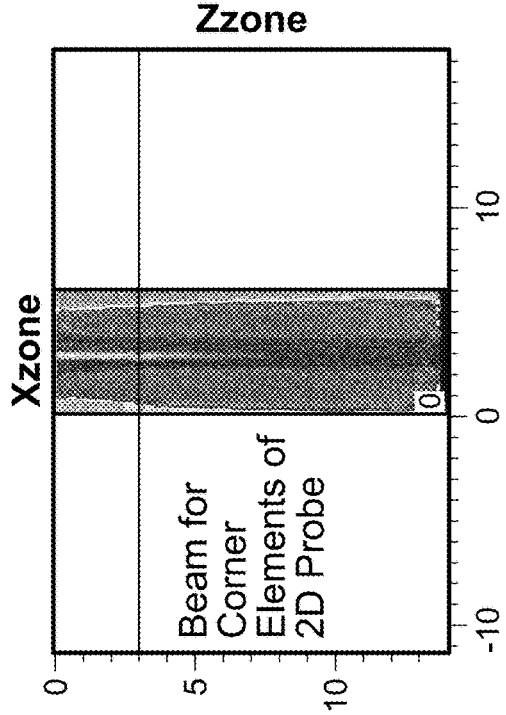
Figure 7D:
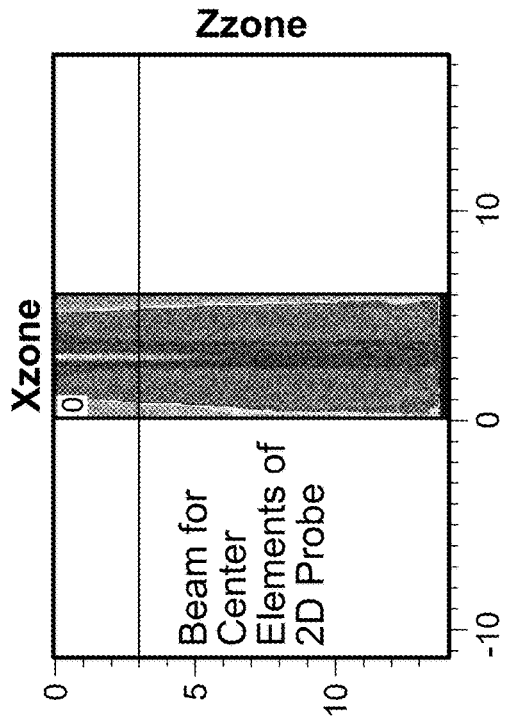

The design of the three-dimensional probe permits inspection of a larger physical area with a smaller probe, thereby allowing for improved probe access as well as a wider coverage area compared to two-dimensional designs. The three-dimensional geometrical arrangement provides optimized accuracy and sensitivity in particular regions of the weld joint. As illustrated by FIGS. 7*a-d*, the result of corner elements of the three-dimensional curved probe shown in FIG. 7*a* illustrates that the beam launch angle is more steered to the normal direction of the typical spot weld indentation when compared to the two-dimensional flat probe case shown in FIG. 7*c*. There is no noticeable change in the beam quality for the center elements for both three-dimensional (FIG. 7*b*) and two-dimensional (FIG. 7*d*) probes. Without losing the high fidelity of inspection capability with the two-dimensional matrix phased array probe, the three-dimensional probe extends the coverage area from the built-in curvature of the probe itself. This invention therefore allows inspection of a larger weld area with a smaller probe diameter, allowing improved access. It may also allow use of fewer numbers of elements, reducing overall system cost, while still covering the entire weld area.

Figure 8:
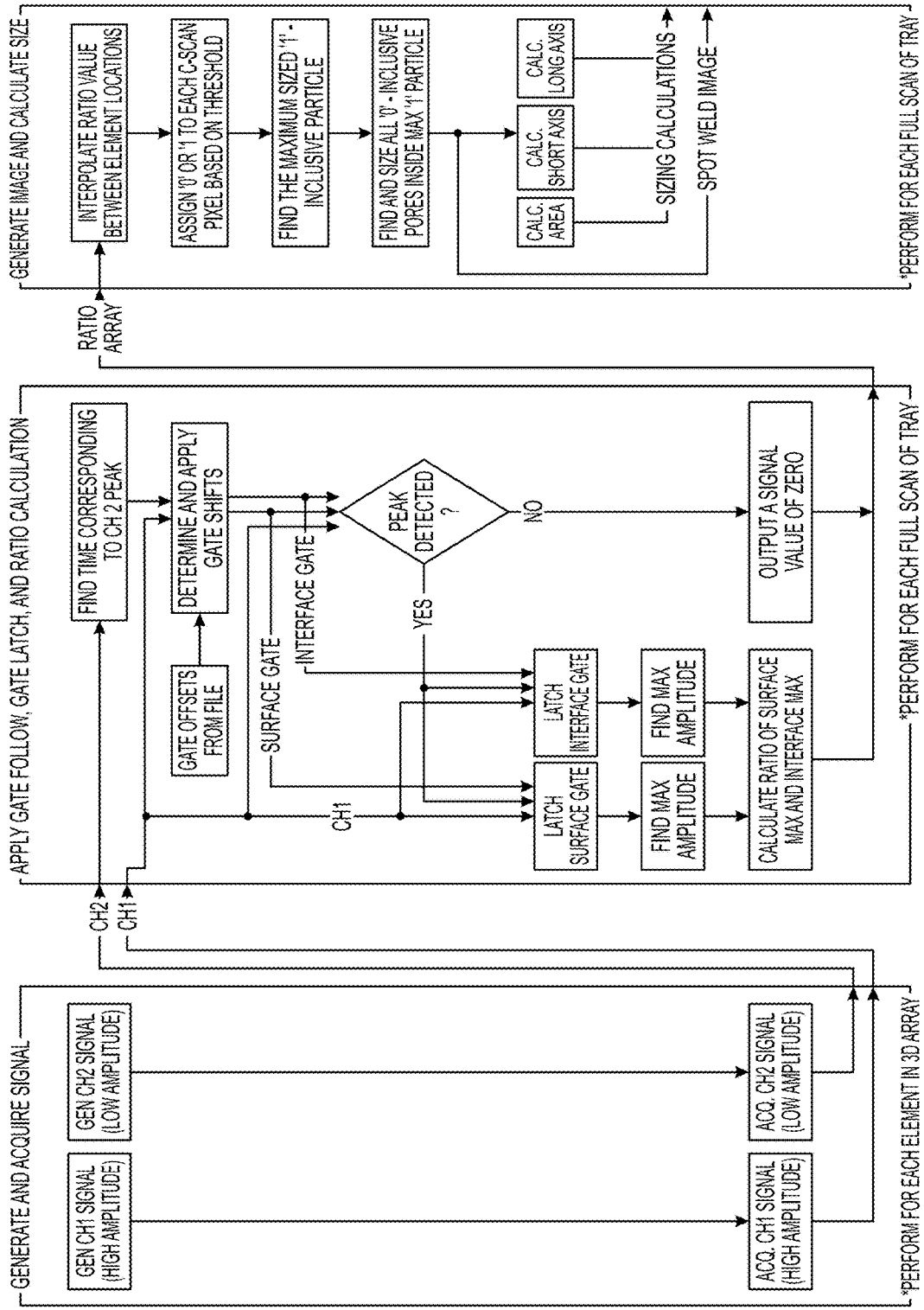
FIG. 8 provides a data flow chart for an exemplary embodiment of the spot weld inspection process of the present invention.
Figure 9:
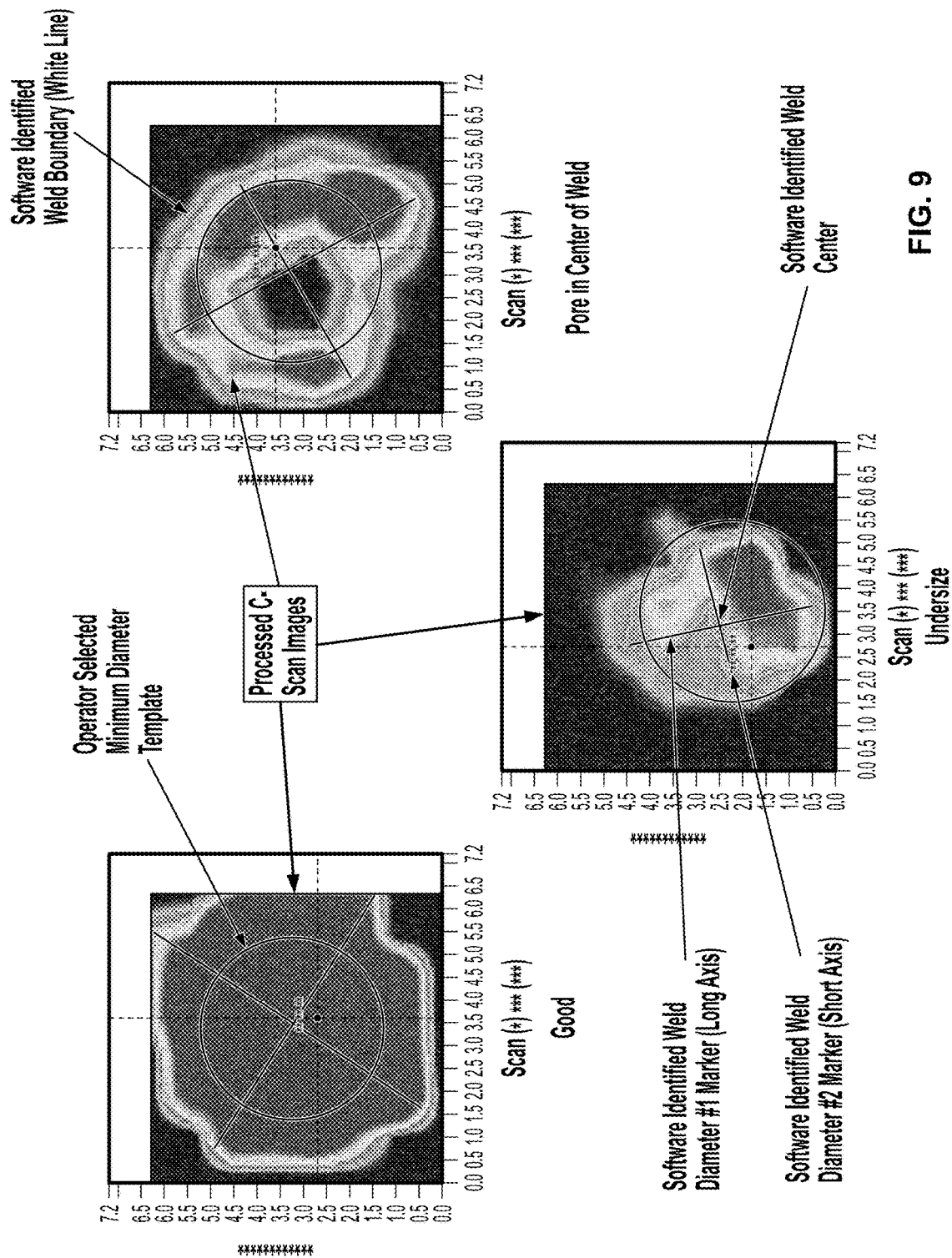
FIG. 9 provides examples of imaging results for various spot weld conditions.

In various embodiments of this invention, a computerized controller is coupled to acoustic probe 100 and transducer elements 106 for directing transmission of the ultrasonic signals and for summing and receiving responses therefrom. With general reference to FIG. 8 (which provides a flowchart that illustrates the function of one possible operating system), the controller is operative to (i) generate and acquire acoustic signals; (ii) detect the surface of the spot weld for each element grouping; (iii) adjust instrument gating to compensate for surface profile and differences in probe orientation; (iv) measure the signal amplitude ratio between responses reflected from the un-bonded areas and areas with good bond; (v) recognize a subset of the responses as being reflected from the un-bonded areas associated with the spot weld and to separate the subset from a remainder of the responses; (vi) measure the extent of the non-delamination dimensions; and (vii) present a two-dimensional color coded image of non-delamination of the spot weld (see FIG. 9). In summary, some of the distinct advantages of this invention include: (i) a three-dimensional matrix probe element; (ii) a phase delay with sub-element group to form a beam focusing and steering capability; (iii) conformable membrane (no need for an attenuation correction); and (iv) an image process utilizing electronic gates to filter out unwanted reflections.

Figure 10:
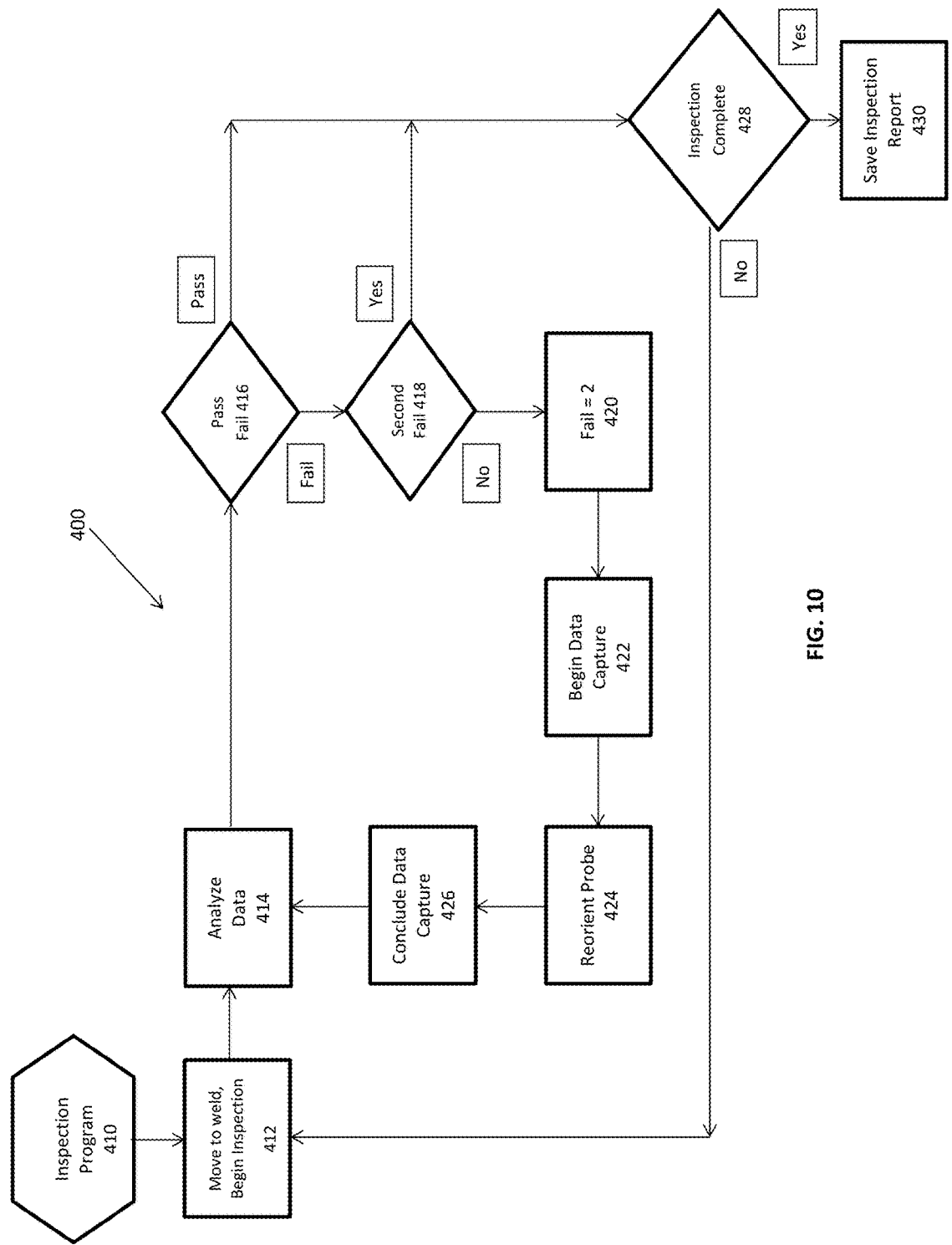
FIG. 10 provides a flow chart depicting the manner in which the automated version of this system permits further action based on evaluation of pre-determined criteria of scan verdicts.
Figure 11:
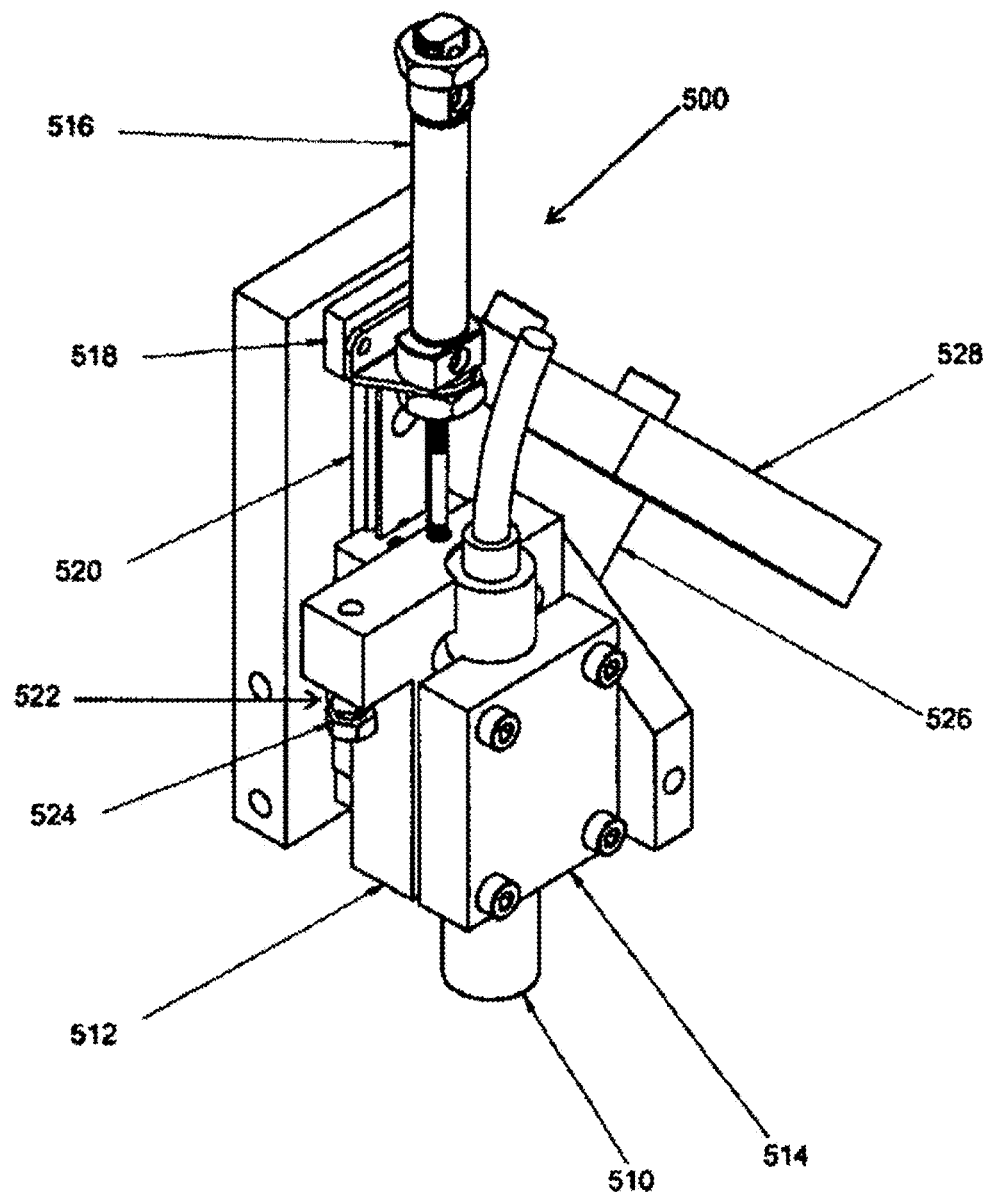
FIG. 11 is a perspective view of the probe-retaining fixture component of an exemplary embodiment of the present invention.

With reference to FIGS. 10-11, the present invention may be configured for manual operation or as a fully automated system. The manual configuration involves manual operation of the inspection probe as well as operation of the user interface. This embodiment relies on the operator of the system for locating the weld to be characterized and then physically manipulating the probe to provide an adequate scan for evaluation. In preparation for inspection, an operator also selects specific parameters for each individual weld and then monitors probe feedback to identify an acceptable scan before capturing a suitable image for actual evaluation. Because the system is typically used to inspect a large number of welds, manual inspection of every weld by an operator is likely to be inefficient and impractical. Accordingly, the automated version of this invention permits inspection of numerous welds with reduced or eliminated operator input by automating many of the tasks of the operator. The automated embodiment permits inspection parameters to be selected remotely based on electronic input from control equipment. In this embodiment, inspection parameters for different metal thicknesses, alloys, layers of stackup, or other relevant conditions may be selected for inspection without input from an operator. Additionally, parameters can be changed as needed for each weld, and for each different workpiece that is inspected.

Regarding motion and signal capture/analysis, a single path sequence is utilized, once the probe is placed on the weld, scanning occurs. However, if the proper scan isn't recognized, a second programmable motion is utilized. The probe is placed on a weld by means of a mechanical actuator, which is further capable of rotating the probe around the point of contact in order to vary the angle of the probe to the work surface. On initial contact, an inspection "scan" is completed, wherein each probe element is triggered, and resultant ultrasonic measurement data from each element is used to construct a C-scan image or output data representing information of the type contained in a C-scan. The C-scan image displays (or the outputted data represents) regions of successful welding, where the weld penetrates all layers of the workpiece, as well as areas where penetration is not complete. At least one algorithm evaluates measurement data to construct an outline of the weld, then determines characteristics of the weld, taking into account the measured perpendicularity of the probe to the workpiece, measured outline of the weld, and internal voids. Software delivers a pass/fail signal based on pre-determined, operator defined criteria of weld, including maximum or minimum diameter, cross-sectional area, perimeter, shape, or inclusion of voids. The pass/fail conclusion is then used to evaluate the need for further inspection. In the event further inspection is warranted, the system manipulates the probe through additional positions likely to produce scans of the part which better represent the condition of the weld. All of these additional scans are stored for further evaluation. At the completion of the additional moves, all captured scans are evaluated in the same way as the first scan, and a pass/fail "verdict" established for each one. The system allows further action based on evaluation of pre-determined criteria of scan verdicts. Measured weld characteristics, including but not limited to weld diameter, are made available for pass/fail decisions, and storage in an external disk drive or other storage medium.

FIG. 10 provides a flow chart depicting a specific exemplary process/method 400 by which the automated version of this system permits further action based on evaluation of pre-determined criteria of scan verdicts. In this example, an inspection program is selected at step 410, the probe is moved to the weld and inspection begins at step 412, weld data is analyzed at step 414, and a pass/fail determination is made. If the inspected weld passes, the system moves on to completion of the process at step 428 and an inspection report is generated and saved at step 430. If the inspected weld fails at step 416, a second fail determination is made at step 418. If the inspected weld fails a second time at step 418, the system moves on to completion of the process at step 428 and an inspection report is generated and saved at step 430. If the inspected weld does not fail a second time at step 418, a determination that further inspection is needed is made at step 420. Data capture then begins at step 422, the ultrasonic probe is reoriented at step 424, data capture is concluded at step 426, and data analysis begins again at step 414 until a determination of weld quality is eventually completed.

In the automated embodiment, the inspection probe is placed on a weld joint by means of a pneumatic cylinder, robotic actuator, or other mechanical device; thereby eliminating the need for a human operator to manually move the probe from weld to weld. Using external commands, the ultrasonic elements in the probe are activated and images (i.e., scans) of the weld being inspected are generated. For the purpose of duplicating the function of an operator manipulating the probe in search of an acceptable scan, an automated actuator moves the probe through a range of positions likely to produce acceptable results. Scan data and images generated during the search are saved for further processing and upon receiving an external command the system reviews captured images according to criteria that are based on automatically selected inspection parameters. Exemplary characteristics to be reviewed may include measured diameter of weld at various locations; total area of weld penetration; weld perimeter; weld shape; or combinations thereof. Also relevant is measured normality to workpiece surface based on reflections of ultrasonic signals at disparate elements in the probe. Selected data is evaluated for quality of the weld joint and measured weld quality can be used for additional inspection of an even wider range of moves, or to label a weld as acceptable or unacceptable.

In an exemplary embodiment, the automated version of the present invention includes a probe mounted on or retained by a device, referred to herein as "fxiture" having a slide that provides compliance necessary for accommodating variations of part shape and location. This compliance allows the probe to be applied to the surface to be inspected with a known force, which is constant across a wide range of displacements. Pressure is also controllable, as the inspection probe utilizes pressure within a specific range. The travel extends far enough to prevent damage to the probe in the event of a collision. With reference to FIG. 11, an exemplary embodiment of the present invention includes fixture 500, which retains ultrasonic probe 510, and that further includes probe cradle 512, clamp block 514, compliant cylinder 516, linear rail assembly 520, travel stop 522, fastener 524, frame 526, and mounting flange 528.

Maintenance of existing probes is labor intensive. Existing probes utilize custom-cut membranes held into the probe cap by a threaded retainer ring. The cap is then threaded onto the probe while immersed in couplant to prevent the inclusion of air bubbles inside the cap. Automation of ultrasonic weld inspection in high-volume applications will involve rapid replacement of probe tips by unskilled labor, or fully automatic tip change. In this invention, probe cap design permits couplant to be trapped in the cap as it fitted to the probe. The design further seals the couplant between the probe and the membrane before it is fully seated, leading to a measured increase of pressure in the fluid as it is fully seated on the probe and engages retaining features. The increase in pressure causes the flexible membrane at the tip of the fluid filled chamber to bulge away from the probe tip and allowing the membrane to conform to the shape of the weld contoured surface as necessary.

This embodiment of the present invention includes the ability to automatically replace the probe tip. The probe tip is designed to be simple to apply, thereby lending itself to automated replacement. The probe design includes a means to replace liquid-filled tip without the use of a threaded connection. The probe tip is pre-filled with couplant, and attached to the probe body by a quick disconnect feature. A quick-disconnect feature may include a plastic cap with molded-in features to engage mating features on the probe body, or steel body with ball detent engagement with the probe body, or locking engagement with minimum (¼-½)

rotational turn. These features also permit replacement by an operator with minimal training and facilitate possible automated replacement.

The system software supports the inclusion of an automated tip replacement by performing a continual automated "self-test" routine that confirms that sound energy is being transmitted through the fluid filled chamber. The software utilizes the sound energy signal from a single defined element or for a group of defined elements, or from number of individual elements with the same automated "self-test" result. The software will confirm transmission of sound energy through the fluid fill chamber in a number of ways, including, for example, comparing the time range in microseconds between the initial signal reflection as the sound exits the probe and the first reflected signal created by the surface of the inspected material, against a known variable time when the first reflected signal is expected. This time is generally a function of the length of the fluid chamber and the protrusion of the bulging flexible membrane. If the first reflected signal does not occur within the anticipated time in microseconds then the system will send a "confirm" signal asking the operator or automated system to confirm that the probe has been positioned against the material to be inspected. Upon receiving a "positive confirmation" that the probe is in position, the system will again look for the time in microseconds between the initial signal reflection as the sound exits the probe and the first reflected signal created by the surface of the inspected material. If the first reflected signal does not occur within the necessary time range, the system will again request confirmation that the probe has been positioned against the material to be inspected. If the system cannot confirm that the first reflected signal occurs within the allotted time range, then the system will send an error signal to the operator or automated system that indicates that the probe tip may require replacement.

The system can also perform automated self-testing by simply confirming that the expected first "spike" within the A-Scan has occurred. This "spike" of the first reflected signal occurs when the sound energy encounters the inspected material. The first reflected signal is already utilized within the system software algorithm(s) and if it is not present then the system interrogation and reporting capabilities will not occur. If the interrogation and reporting cannot occur, as expected, then the system will request a confirmation that the probe has been positioned against the material to be inspected. After a set number of iterations of "test" and "confirm positioning", the system will send an error signal to the operator or automated system that indicates that the probe tip may require replacement.

The system software can specifically utilize the first reflected signal to confirm that the fluid filled chamber is functioning correctly by utilizing the existing algorithm that defines the positioning of the "gates". After the probe is positioned against the material to be inspected, the algorithm will position the first "gate" at a specific and variable distance in microseconds beyond the center point of the A-Scan peak. If an A-scan is not occurring, the gates will not be adjusted. This gate adjustment occurs for each element of the probe and occurs continuously. If this specific algorithm is unable to function, after it is known that the probe has been positioned against the material to be inspected, then the system will send an error signal to the operator or automated system that indicates that the probe tip may require replacement. The system software may also look for the initial signal reflection as the sound exits the probe and the reflected signal as the sound passes the flexible membrane at the probe tip. This signal at the probe tip is not as strong as the reflected single received from the inspected material surface.

Important aspects of this invention in include: (i) automated triggering of the ultrasonic inspection unit; (ii) the storage of multiple scans; (iii) judging quality of stored scans based on weld characteristics and measured normality to surface; (iv) selection of best data; (v) evaluation of recorded data; (vi) output of result in a manner usable to automated equipment (robot, data server, Programmable Logic Controller); and (vii) replaceable probe tip, particularly the bonded membrane component of the tip. While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A system for non-destructively evaluating spot welds, comprising:
   (a) at least one matrix phased array probe, wherein the matrix phased array probe includes:
      (i) a plurality of ultrasonic transducer elements arranged in a curved array at one end of the probe, wherein the transducer elements are operative to both generate ultrasonic signals and receive reflections thereof; and
      (ii) a combination of materials for allowing the probe to conform to a contoured surface of a spot weld while enabling sound energy to be transferred directly into the spot weld under test conditions, wherein the combination of materials further includes a flexible membrane mounted on a tip of the probe and a fluid filled chamber or solid sound delay material disposed between the membrane and the array;
   (b) a fixture adapted to be mounted on a robot or other mechanical actuator, wherein the fixture is further adapted to retain the at least one matrix phased array probe; and
   (c) an enclosure, wherein the enclosure further includes:
      (i) at least one input for connecting to the at least one matrix phased array probe;
      (ii) ultrasonic phased array transmitting and receiving circuitry in electrical communication with the at least one input;
      (iii) at least one data processor running software that includes at least one algorithm for processing data received from the probe and generating discrete specifications of evaluated welds, wherein the discrete specifications further include pass indications or fail indications regarding weld acceptability; and
      (iv) at least one output for outputting the discrete specifications of the evaluated welds.

2. The system of claim 1, wherein the transducer elements are further arranged into discrete subgroups, and wherein each subgroup may be activated independently of the other subgroups and at different time intervals.

3. The system of claim 2, wherein activating each subgroup independently of the other subgroups and at different time intervals for each of the transducer elements in the subgroup provides signal focusing and steering capability.

4. The system of claim 1, wherein the ultrasonic phased array transmitting and receiving circuitry further includes 64-channel phased array circuitry with 16-channel simultaneous multiplexing capability.

5. The system of claim 1, wherein the software further includes inputs that permit calibration of the system by using the matrix phased array probe to initially scan a weld joint of known diameter and then adjust system gating ratios accordingly.

6. The system of claim 1, wherein the robot or other mechanical actuator is operative to move the probe through a predetermined range of positions, and wherein the predetermined range of positions is operative to facilitate production of high-integrity scans of welds being characterized.

7. The system of claim 1, wherein the robot or other mechanical actuator includes a slide, and wherein the slide provides compliance for accommodating variations in shape and location of welded parts, and further wherein the compliance allows the probe to be applied to a weld surface to be inspected with a predetermined force that is constant across a predetermined range of displacements.

8. The system of claim 1, wherein the at least one matrix phased array probe is operative to determine physical characteristics of a weld being examined, and wherein the physical characteristics include measured weld diameter at various locations within the weld, total area of weld penetration, weld perimeter, weld shape, or combinations thereof.

9. The system of claim 1, wherein the at least one matrix phased array probe is operative to measure normality to workpiece surface based on the reflections of the ultrasonic signals at disparate elements within the probe.

10. The system of claim 1, wherein the tip of the probe is pre-filled with a couplant, and wherein the pre-filled tip further includes a quick-connect disconnect mechanism for rapidly detaching and reattaching the tip to the probe.

11. The system of claim 10, wherein the software generates notifications when the tip of the probe requires replacement.

12. A system for non-destructively evaluating spot welds, comprising:
  (a) at least one matrix phased array probe, wherein the matrix phased array probe includes:
    (i) a plurality of ultrasonic transducer elements arranged in a curved array at one end of the probe, wherein the transducer elements are operative to both generate ultrasonic signals and receive reflections thereof, and wherein the transducer elements are further arranged into discrete subgroups, and wherein each subgroup may be activated independently of the other subgroups and at different time intervals; and
    (ii) a combination of materials for allowing the probe to conform to a contoured surface of a spot weld while enabling sound energy to be transferred directly into the spot weld under test conditions, wherein the combination of materials further includes a flexible membrane mounted on a tip of the probe and a fluid filled chamber or solid sound delay material disposed between the membrane and the array;
  (b) a fixture adapted to be mounted on a robot or other mechanical actuator, wherein the fixture is further adapted to retain the at least one matrix phased array probe, wherein the robot or other mechanical actuator is operative to move the probe through a predetermined range of positions, and wherein the predetermined range of positions is operative to facilitate production of high-integrity scans of welds being characterized; and
  (c) an enclosure, wherein the enclosure further includes:
    (i) at least one input for connecting to the at least one matrix phased array probe;
    (ii) ultrasonic phased array transmitting and receiving circuitry in electrical communication with the at least one input;
    (iii) at least one data processor running software that includes at least one algorithm for processing data received from the probe and generating discrete specifications of evaluated welds, wherein the discrete specifications further include pass indications or fail indications regarding weld acceptability; and
    (iv) at least one output for outputting the discrete specifications of the evaluated welds.

13. The system of claim 12, wherein activating each subgroup independently of the other subgroups and at different time intervals for each of the transducer elements in the subgroup provides signal focusing and steering capability.

14. The system of claim 12, wherein the ultrasonic phased array transmitting and receiving circuitry further includes 64-channel phased array circuitry with 16-channel simultaneous multiplexing capability.

15. The system of claim 12, wherein the software further includes inputs that permit calibration of the system by using the matrix phased array probe to initially scan a weld joint of known diameter and then adjust system gating ratios accordingly.

16. The system of claim 12, wherein the robot or other mechanical actuator includes a slide, and wherein the slide provides compliance for accommodating variations in shape and location of welded parts, and further wherein the compliance allows the probe to be applied to a weld surface to be inspected with a predetermined force that is constant across a predetermined range of displacements.

17. The system of claim 12, wherein the at least one matrix phased array probe is operative to determine physical characteristics of a weld being examined, and wherein the physical characteristics include measured weld diameter at various locations within the weld, total area of weld penetration, weld perimeter, weld shape, or combinations thereof.

18. The system of claim 12, wherein the at least one matrix phased array probe is operative to measure normality to workpiece surface based on the reflections of the ultrasonic signals at disparate elements within the probe.

19. The system of claim 12, wherein the tip of the probe is pre-filled with a couplant, and wherein the pre-filled tip further includes a quick-connect disconnect mechanism for rapidly detaching and reattaching the tip to the probe.

20. The system of claim 19, wherein the software generates notifications when the tip of the probe requires replacement.

21. A system for non-destructively evaluating spot welds, comprising:
  (a) at least one matrix phased array probe, wherein the matrix phased array probe includes:
    (i) a plurality of ultrasonic transducer elements arranged in a curved array at one end of the probe, wherein the transducer elements are operative to both generate ultrasonic signals and receive reflections thereof; and wherein the transducer elements are further arranged into discrete subgroups, and wherein each subgroup may be activated independently of the other subgroups and at different time intervals; and (ii) a combination of materials for allowing the probe to conform to a contoured surface of a spot weld while enabling sound energy to be transferred directly into the spot weld under test conditions, wherein the combination of materials further includes a flexible membrane mounted on a tip of the probe and a fluid filled chamber or solid sound delay material disposed between the membrane and the array, and wherein the tip of the probe is pre-filled with a couplant, and further includes a quick-connect disconnect mechanism for rapidly detaching and reattaching the tip to the probe; and (b) a fixture adapted to be mounted on a robot or other mechanical actuator, wherein the fixture is further adapted to retain the at least one matrix phased array probe, wherein the robot or other mechanical actuator is operative to move the probe through a predetermined range of positions, and wherein the predetermined range of positions is operative to facilitate production of high-integrity scans of welds being characterized; and (c) an enclosure, wherein the enclosure further includes:
  (i) at least one input for connecting to the at least one matrix phased array probe;
  (ii) ultrasonic phased array transmitting and receiving circuitry in electrical communication with the at least one input;
  (iii) at least one data processor running software that includes at least one algorithm for processing data received from the probe and generating discrete specifications of evaluated welds, wherein the discrete specifications further include pass indications or fail indications regarding weld acceptability; and
  (iv) at least one output for outputting the discrete specifications of the evaluated welds.

22. The system of claim 21, wherein activating each subgroup independently of the other subgroups and at different time intervals for each of the transducer elements in the subgroup provides signal focusing and steering capability.

23. The system of claim 21, wherein the ultrasonic phased array transmitting and receiving circuitry further includes 64-channel phased array circuitry with 16-channel simultaneous multiplexing capability.

24. The system of claim 21, wherein the software further includes inputs that permit calibration of the system by using the matrix phased array probe to initially scan a weld joint of known diameter and then adjust system gating ratios accordingly.

25. The system of claim 21, wherein the robot or other mechanical actuator includes a slide, and wherein the slide provides compliance for accommodating variations in shape and location of welded parts, and further wherein the compliance allows the probe to be applied to a weld surface to be inspected with a predetermined force that is constant across a predetermined range of displacements.

26. The system of claim 21, wherein the at least one matrix phased array probe is operative to determine physical characteristics of a weld being examined, and wherein the physical characteristics include measured weld diameter at various locations within the weld, total area of weld penetration, weld perimeter, weld shape, or combinations thereof.

27. The system of claim 21, wherein the at least one matrix phased array probe is operative to measure normality to workpiece surface based on the reflections of the ultrasonic signals at disparate elements within the probe.

28. The system of claim 21, wherein the software generates notifications when the tip of the probe requires replacement.

29. The system of claim 21, further comprising at least one remote monitor for displaying color coded ultrasonic C-scan images of the welds being characterized, in real time.

30. The system of claim 29, wherein the color coded ultrasonic C-scan images further include an average diameter of weld nugget and a fused area for each of the welds being characterized.

* * * * *